United States Patent [19]

Harano

[11] Patent Number: 4,465,873
[45] Date of Patent: Aug. 14, 1984

[54] PROCESS FOR OBTAINING BUTANEDIOLS

[75] Inventor: Yoshiyuki Harano, Himeji, Japan

[73] Assignees: Daicel Chemical Industried, Ltd., Sakai; Kuraray Co., Ltd., Kurashiki, both of Japan

[21] Appl. No.: 511,419

[22] Filed: Jul. 6, 1983

[30] Foreign Application Priority Data

Jul. 7, 1982 [JP] Japan ................................ 57-117945

[51] Int. Cl.³ ...................... C07C 29/80; C07C 31/20; C07C 29/88
[52] U.S. Cl. ...................................... 568/868; 568/862
[58] Field of Search ............................... 568/862, 868

[56] References Cited

U.S. PATENT DOCUMENTS

| 4,064,145 | 12/1977 | Taylor | 568/862 |
| 4,083,882 | 4/1978 | Taylor et al. | 568/862 |
| 4,154,970 | 5/1979 | Beer et al. | 568/868 |
| 4,200,501 | 4/1980 | Panek et al. | 568/868 |
| 4,263,449 | 4/1981 | Saito et al. | 568/862 |
| 4,298,766 | 11/1981 | Broecker et al. | 568/862 |

FOREIGN PATENT DOCUMENTS 210851  4/1968  U.S.S.R. .............................. 568/868

Primary Examiner—J. E. Evans
Attorney, Agent, or Firm—Flynn, Thiel, Boutell & Tanis

[57] ABSTRACT

A process is disclosed for obtaining butanediols by distilling the same from an aqueous solution obtained by hydrogenation, carried out in the presence of a nickel catalyst, of a hydroformylated allyl alcohol. The invention process is characterized in that 2-methyl-1,3-propanediol, 1,4-butanediol and a high-boiling fraction are separated by distillation from a butanediol mixture obtained using the following steps:

(1) the aqueous solution is treated such that the pH of the aqueous solution is adjusted to 8.5 or above, and precipitates thus formed are removed;
(2) the aqueous solution is treated such that residual 4-hydroxybutyraldehyde and water are distilled off at a temperature of up to 100° C.; and
(3) the resulting mixture is heated at a temperature of up to 180° C. to obtain a distillate consisting of 2-methyl-1,3-propanediol and 1,4-butanediol, free of the high-boiling fraction.

12 Claims, 2 Drawing Figures

PROCESS FOR OBTAINING BUTANEDIOLS

The present invention relates to a process for obtaining high-quality butanediols. In the present specification, the term "butanediol" means diols having four carbon atoms.

It is well known to produce butanediols by the hydrogenation of a hydroformylated product of allyl alcohol, in the presence of a nickel catalyst. For example, the specification of Japanese patent publication No. 19563/1978 discloses a process for obtaining two butanediols, namely, 1,4-butanediol (hereinafter referred to as 1,4-BG) and 2-methyl-1,3-propanediol (hereinafter referred to as MPG), by catalytically hydrogenating, in the presence of a Raney nickel catalyst, an aqueous solution of a reaction product comprising hydroxybutyraldehydes, i.e., 4-hydroxybutyraldehyde (hereinafter referred to as HBA) and 3-hydroxy-2-methylpropionaldehyde (hereinafter referred to as HMPA). This solution was obtained by reacting allyl alcohol with a synthesis gas ($H_2+CO$), in the presence of a rhodium-containing catalyst, in an organic solvent, such as benzene, and then separating out the rhodium catalyst by extraction with water.

In conventional processes for obtaining butanediols from the above aqueous solution, water and by-products having low boiling points are distilled off and then MPG, having a boiling point of 213° C., and 1,4-BG, having a boiling point of 230° C., are obtained separately by distillation, taking advantage of the difference in the boiling points of 1,4-BG and MPG.

However, in the treatment of the butanediol mixture obtained by the catalytic hydrogenation of hydroxybutyraldehyde, two problems have been posed. One of these problems is that the separation of the two butanediols by distillation is far more difficult than is expected based on the difference in their boiling points. The other problem is that 1,4-BG and MPG that are isolated by the distillation have offensive smells.

After investigations made for the purpose of solving these problems, which problems were not recognized in the prior art, the inventors have discovered that the unanticipated difficulty of separating MPG and 1,4-BG is due to the presence of impurities peculiar to the hydrogenation of hydroxybutyraldehydes, and that these impurities are formed, together with other impurities which cause the offensive smells of the products, mainly in a heating step during the purification. The inventors have succeeded in obtaining 1,4-BG and MPG of high quality and free of offensive smell by preventing the production of the impurities which cause the above problems by employing new measures in the purification step.

Thus, the present invention provides a process for obtaining butanediols by distilling the same from an aqueous solution obtained by hydrogenation, carried out in the presence of a nickel catalyst, of a hydroformylated product of allyl alcohol, in which 2-methyl-1,3-propanediol, 1,4-butanediol and a high-boiling fraction comprising impurities having boiling points higher than the boiling points of the butanediols are separated by distillation from a butanediol mixture obtained by a process including the following steps:

(1) the aqueous solution containing 1,4-BG and MPG is treated so that the pH of the aqueous solution is adjusted to 8.5 or above, and precipitates thus formed are removed;

(2) the 4-hydroxybutyraldehyde remaining in said solution is then distilled off at a temperature of up to 100° C.; and (3) the resulting mixture is treated to a temperature of up to 180° C. to distill 2-methyl-1,3-propanediol and 1,4-butanediol, said high-boiling impurities being left behind. The resulting mixture can then be distilled again to separately obtain 2-methyl-1,3-propanediol and 1,4-butanediol, or the butanediols may be collected separately during step (3).

Figure 1:
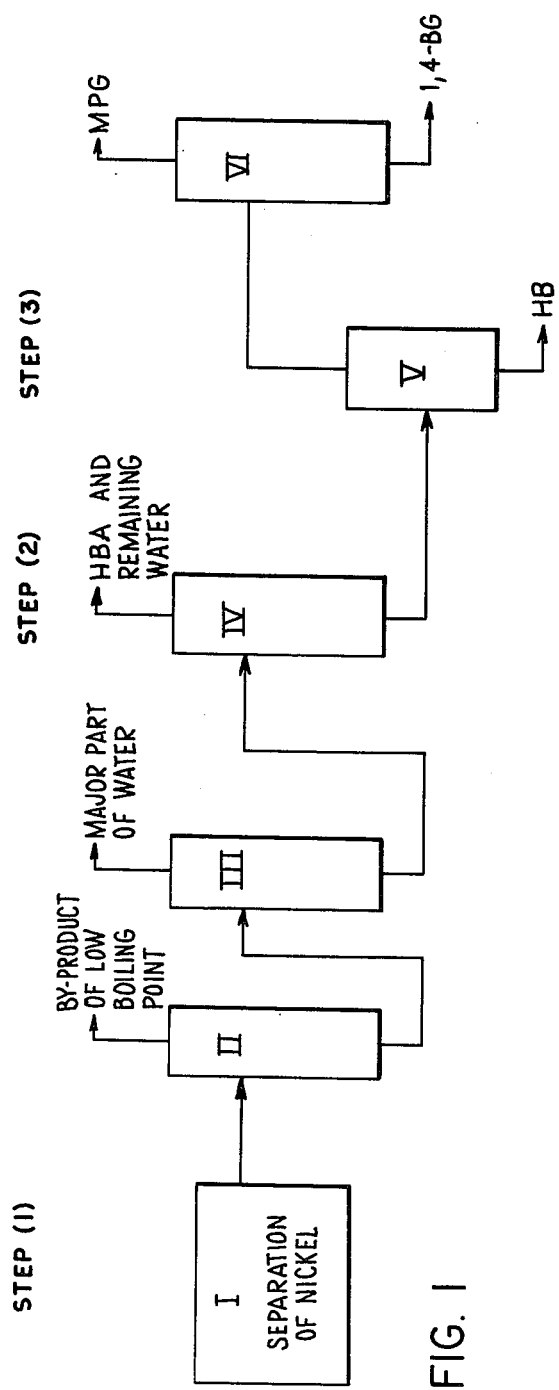
FIG. 1 shows a flow sheet of an example of the invention process. I is the step (1). II and III are the concentration step. IV is the step (2). V is the step (3). VI is the separation step of the final products.

It has been found that the impurities, which interfere with the separation of MPG and 1,4-BG by distillation, include two 2-hydroxytetrahydrofuran ethers, namely, 2-(3-hydroxy-2-methylpropoxy)tetrahydrofuran (hereinafter referred to as HMPTHF) and 2-(4-hydroxybutoxy)tetrahydrofuran (hereinafter referred to as HBTHF). The presence of HMPTHF makes the separation of MPG and 1,4-BG quite difficult and often substantially impossible. As one reason for this, it is considered that HMPTHF forms an azeotropic mixture with 1,4-BG, which mixture has a vapor pressure very close to that of MPG. Further, HBTHF also forms an azeotropic mixture with 1,4-BG, which mixture has a boiling point between the boiling points of MPG and 1,4-BG, whereby the separation of MPG and 1,4-BG is made difficult. In addition, both ethers are incorporated in products containing MPG and 1,4-BG made by conventional methods, making the production of high quality butanediols difficult.

Based on the recognition of the presence of impurities which interfere with the separation of butanediols by distillation, the inventors have carried out pertinent investigations and discovered that nickel and hydroxybutyraldehyde remaining in the reaction liquid exert influences on the levels of these impurities.

The aqueous solution containing MPG and 1,4-BG, according to the present invention, is obtained by the hydrogenation of a hydroformylated product of allyl alcohol, in the presence of a nickel catalyst, such as Raney nickel. The aqueous solution has an acidity of about pH 4 to 6, since an acid is generally formed to some extent. The solution contains a relatively large amount (30-50 ppm) of nickel and a small amount of unreacted hydroxybutyraldehyde. Therefore, if MPG and 1,4-BG are to be separated by distillation after the removal of a low-boiling fraction and concentration, the hydroxybutyraldehyde and butanediols (MPG and 1,4-BG) must be heated to 130° to 200° C. for several hours in a butanediol separation column in the presence of the nickel which thereby becomes concentrated from 5- to 7-fold. Nickel becomes further concentrated, generally from 30- to 50-fold, in a step of removing a high-boiling fraction, although the degree of concentration in this step varies depending on the degree of concentration of the high-boiling fraction.

Under these conditions, which are the ones used in the conventional separation techniques for MPG and 1,4-BG, a problem is posed in that part of the concentrated nickel deposits on and stains the apparatus and also tends to clog the apparatus, whereby continuation of the distillation over a long period of time becomes difficult (see Comparative Example 1 given below).

This problem cannot be disregarded in the production of high quality butanediols on an industrial scale, although it is often ignored or overlooked in experiments on a small scale. Having noted this problem, which has not been recognized in the prior art, the inventor attempted to solve this problem by adjusting the pH of the aqueous solution obtained by the hydrogenation reaction to pH 8.5 or higher and then removing the resulting precipitates (step (1)). The nickel content of the hydrogenation reaction liquid is reduced remarkably by making the liquid alkaline by addition of an alkaline substance. For example, even if the hydrogenation reaction liquid containing 60 ppm of Ni is adjusted to pH 7, the liquid still contains 48 ppm of Ni ions. If the pH is adjusted to 8.5 and the resulting precipitates are removed, the Ni content is reduced to 1/3 of its original value, i.e., to 20 ppm. Further, if the pH is adjusted to 9.5, the Ni content of the filtrate is reduced to 3 ppm, such a low nickel content being negligible. Thus, nickel precipitation in the distillation of butanediols, after removal of the low-boiling fraction and concentration, can be prevented, and continuous distillation over a long time period becomes possible as shown in Example 2 below.

It has been further found that, in the separation of MPG and 1,4-BG by distillation, nickel in the reaction system tends to cause production of HMPTHF and HBTHF, in addition to Ni precipitation, and that a large amount of nickel acts as a dehydrogenation catalyst for 1,4-BG, whereby to form an additional amount of hydroxybutyraldehyde and to increase the amount of by-produced HMPTHF and HBTHF.

The effects of the pH control and the removal of the precipitates on the decrease of the content of impurities, through reduction of the nickel content, will be shown below. After the pH was adjusted to 7.5 by addition of an alkaline substance, the liquid in a concentration part of a column for effecting the separation of MPG and 1,4-BG contained about 280 ppm of nickel, corresponding to 40 ppm of nickel in the aqueous solution obtained by the hydrogenation reaction. After the solution was treated to maintain a temperature of 180° C. for 5 h, the HBTHF content thereof was increased from 0.22% to 1.25% and substantially all of the nickel was precipitated. By contrast, when the pH was adjusted to 9.5 followed by removal of the precipitates, the liquid in the concentration part of the column for effecting the separation of MPG and 1,4-BG contained 45 ppm of nickel dissolved therein, and after heating to 180° C. for 5 h, an increase of HBTHF content was scarcely recognized and nickel was scarcely precipitated therefrom. Both liquids contained only a very small amount of 4-hydroxybutyraldehyde before the heating.

In obtaining the intended butanediols having a high quality and a very low impurity content, according to the present invention, from an aqueous solution obtained by the hydrogenation, in the presence of the nickel catalyst, of the hydroformylated product of allyl alcohol, it is effective to adjust the pH of the aqueous hydrogenation reaction solution with an alkali to a pH of 8.5 or above, preferably above 9.5, and to remove the resulting precipitates. It has also been found that, by this treatment, nickel precipitation in the purification apparatus can be prevented and problems, such as staining or clogging of the apparatus, can be avoided as well.

Although the removal of dissolved nickel by pH control as described above in step (1) is a quite effective means for obtaining high-quality butanediols, a further problem with the conventional process has been discovered. This problem is due to the fact that the by-production of HMPTHF and HBTHF is unavoidable in the presence of hydroxybutyraldehyde, even if nickel is not present. In the hydrogenation of the hydroformylated product of allyl alcohol in the presence of the nickel catalyst, a complete conversion of the starting hydroxybutyraldehyde cannot be expected. The hydrogenation reaction liquid contains generally about 0.1 to 0.3 wt. %, based on the butanediols, of hydroxybutyraldehyde. The hydrogenation reaction liquid is generally purified by distilling off the low boiling by-products, such as n-propanol, and then concentrated by evaporating water. These steps are shown as II and III in the drawings, respectively. 4-hydroxybutyraldehyde having a boiling point far higher than that of water, namely about 170° C., is scarcely removed by ordinary evaporation, and it is introduced into the column, shown as VI in the drawings, for effecting separation of MPG and 1,4-BG. The temperature in this column in which high-boiling diols are distilled is as high as, for example 133° to 162° C. at 50 mmHg. In a distillation column at such a high temperature, 4-hydroxybutyraldehyde reacts with butanediols, such as MPG, to form 2-hydroxytetrahydrofuran ethers.

More particularly, after heating a nickel-free liquid containing MPG and 1,4-BG in the column for effecting separation of MPG and 1,4-BG, at 165° C. for 1 h, the HBA content was reduced from 1.15% to 0.02% and the HMPTHF content was increased remarkably from 0.45% to 3.9%. Further, the HBTHF content was also increased from an undetectable amount to 0.41%. The foregoing percentages were determined by peak area percentages in gas chromatography; the same shall apply to percentage amounts given hereafter.

The step (2) provided to counter the formation of the impurities, according to the present invention, is distillation of residual HBA at a temperature of up to 100° C. The temperature to be controlled in the step (2) should be adjusted at a location where HBA actually exists in the distillation system in such an amount as is detectable by a usual analysis, for example 0.01 weight percent or above. It may be acceptable even if the temperature is higher than 100° C. at another location where HBA does not exist in the above mentioned sense, for instance at the bottom of the continuous distillation column. This treatment will be illustrated with reference to the above mentioned aqueous solution and the hereto attached drawings. The solution which has been separated out of nickel by the step (1) is usually, in advance to the step (2), concentrated by evaporation of by-products having low boiling points and a major portion of water. This step is illustrated in the drawings by II and III. The concentration step is, in general, conducted at an ambient pressure or a slightly reduced pressure, from 200 to 300 mmHg. It is preferred that about 10 weight percent of water still remains in the concentrated solution in order to carry out the step (2) effective at so low a temperature as mentioned below. Subsequently to the evaporation step III of a major part of the water, the pressure is further reduced and 4-hydroxybutyraldehyde is distilled off together with the remaining water at a temperature of up to 100° C., preferably 50° to 70° C. The step (2), illustrated in the drawings as IV, is usually effected at a more reduced pressure than the concentration step III. The pressure of the step (2) may be determined so as to maintain the temperature within the above defined range, 100° C. or lower, preferably from 50° to 70° C., at a location where HBA substantially exists in the distillation column. In fact, Example 1, described below, shows that HBA is distilled out together with water from the top of the column where the temperature is so low, but it cannot be detected at the bottom of the column where the temperature is higher than 100° C.

It will be understood from the following example that the formation of HMPTHF or the like can be prevented by maintaining the distillation temperature below 100° C., even when 4-hydroxybutyraldehyde is heated together with the butanediols. When the composition of a butanediol solution heated to 62° C. was examined in the same manner as for the above solution heated to 165° C., the HBA content was 1.11%, which is substantially equal to that in the above-mentioned case, the HMPTHF content was 0.52% and HBTHF could not be detected. Thus, by this method increase of the content of impurities which interfere with the separation of butanediol by distillation is scarcely observed. When the heating temperature was 95° C., the impurity-controlling effect was recognized to some extent, although the results (0.46% HBA, 2.77% HMPTHF and 0.03% HBTHF) were inferior to those obtained when the temperature was 65° C.

The effects of the above-mentioned step (2) are shown in Example 3, in which the formation of HBTHF was prevented by reducing the column bottom temperature to 85° C. On the other hand, the formation of HBTHF was observed in Comparative Example 3 in which the concentration step was performed at 135° C. in the presence of HBA.

MPG, 1,4-BF and a high-boiling fraction are separated by distillation from the butanediol mixture obtained by (1) adjusting the pH of the aqueous hydrogenation reaction solution containing MPG and 1,4-BG to 8.5 or above and removing the resulting precipitates, and then (2) distilling residual 4-hydroxybutyraldehyde at a temperature of up to 100° C. The high-boiling fraction contains substances having high boiling points comprising condensates of aldehydes formed in the step of hydroformylation of allyl alcohol or in the hydrogenation reaction step, which products have boiling points higher than the boiling points of said butanediols. The high-boiling fraction is formed in an amount of generally 0.5 to 1.0% based on the amount of the butanediols. The third characteristic feature of the present invention is that 1,4-BG and MPG are distilled from the high-boiling fraction at a temperature of 180° C. or less to separately obtain butanediols free of offensive smells and having a high quality.

Further reasons why the distillation is effected under the above-mentioned conditions will now be described.

Nickel contained in the hydrogenation reaction liquid, as discussed above, is removed substantially, but not completely, by the step (1). Further, other metal components that are difficult to remove by precipitation caused by pH adjustment might be contained therein. These metal components are concentrated in the purification step together with the high-boiling fraction. For example, even if the dissolved nickel content is reduced to 3 ppm by the pH adjustment and precipitate removal step, it is increased to 150 ppm after the 50-fold concentration in the high-boiling fraction removal step. A catalytic reaction occurs in a high temperature region at the bottom of the distillation column, in which butanediols and the high-boiling by-products are heated in the presence of the concentrated metal. This reaction poses two problems. The first problem is that the butanediols distilled off exhibit an offensive smell due to a newly formed low-boiling fraction formed by the decomposition of the high-boiling fraction. The other problem is the formation of HBA by the dehydrogenation of 1,4-BG. HBA reacts with the butanediols to form impurities, such as HMPTHF and HBTHF, which deteriorate the separability of the butanediols. This fact is concretely shown by Comparative Example 2 below.

Generally speaking, separation of a high boiling substance is conducted by heating for a long period of time. Nevertheless, the invention can be attained at a temperature as low as 180° C. or lower. Accordingly the invention prevents the formation of impurities which would diminish the separability of the offensive smell-emitting substances and the intended butanediols. Of course it would be better to make the residence time as short as possible at a temperature of 180° C. or lower and thereafter minimize the heating time of the intended products. For example, after the removal of nickel from the hydrogenation reaction liquid by the pH adjustment step and subsequent removal of the precipitate, followed by removal of the low-boiling fraction, water and HBA, the liquid is treated in an evaporation device having a small liquid-holding capacity, such as a thin film evaporator, to evaporate the butanediols at a temperature of up to 180° C., preferably up to 170° C., in a short time, whereby the butanediols are separated from the high-boiling fraction.

Since the difference in relative volatility between the high-boiling fraction and the butanediols is sufficient, the former can be separated from the latter sufficiently by a simple flash evaporation of the butanediols. From the viewpoint of the yield of the butanediols, it is advantageous to concentrate the high-boiling fraction as much as possible. By such concentration, however, the amount of the high-boiling fraction at the bottom of the evaporator is reduced. Consequently, the residence time in the evaporator is prolonged and, therefore, it is preferred to use an evaporation device having a small liquid-holding capacity, such as a thin film evaporator.

After the separation of the butanediols from the high-boiling fraction at a temperature of up to 180° C., followed by the separation of MPG from 1,4-BG by distillation, high-quality butanediols are obtained. In the separation of MPG, 1,4-BG and a high-boiling fraction by distillation, it is most desirable to remove the high-boiling fraction first before separating MPG and 1,4-BG. Although it is essentially possible to separate MPG first, then 1,4-BG and the high-boiling fraction by distillation, the residence time of the liquid in the high temperature zone is prolonged by this method.

In the present invention, the butanediol mixture should be distilled in a substantially water-free state after the above steps (1) and (2), since a greater amount of energy is required for the separation from the high-boiling fraction if this step is effected prior to the removal of the water by distillation.

Figure 2:
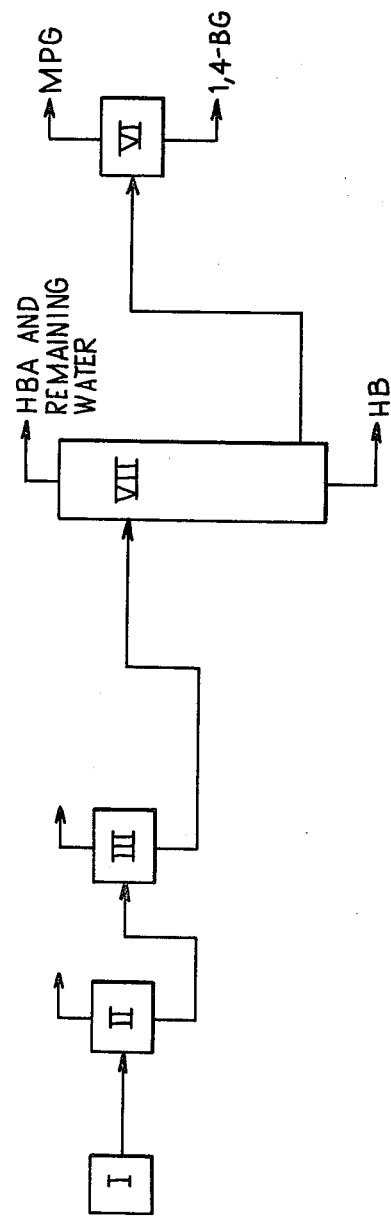
FIG. 2 indicates another example of the invention in which the steps IV and V are combined with each other to a single step VII.

It is also possible to effect the separation of the high-boiling fraction simultaneously with the above treatment (2). In other words, it is possible to distill off the remaining water and HBA at the top of the column at a temperature of up to 100° C., and to distill off the butanediol mixture in vapor form at a position close to the bottom of the column, which contacts the gaseous phase, for instance the gaseous phase of the reboiler, to which position the butanediol mixture subjected to the treatment (2) flows down. Such combined step VII of the steps IV and V is shown in FIG. 2. Since the columns IV and VII differ from each other with respect to the composition of the bottom liquid, the column VII must have a lower pressure than the column IV in order to maintain the temperature at the bottom within the determined range, 180° C. or lower. The top pressure of the column VII is required to be further reduced according to the pressure drop in the column, to a pressure of not higher than 50 mmHg, for example from 20 to 40 mmHg. In this way, the distillant from the top of the column VII contains a large amount of water which easily evaporates. Such distillant is required to be cooled by not water at a normal temperature, but chilled water at about 10° C. This combined method is practicable because the equipment gets more simple, even though the cooling is so expensive.

If an ion exchange resin is used for removing metals from the solution, the formation of substances emitting an offensive smell cannot be prevented. The step (3) of removing the remaining high-boiling organic substance at a temperature of up to 180° C. is critical for obtaining high-quality butanediols.

An embodiment of the process of the present invention wherein the combination of the above-mentioned three treatments is employed is as follows. After the hydrogenation, the pH of the aqueous solution is adjusted to 9.5 or higher, the precipitate thus formed is removed, and a low-boiling fraction, such as n-propanol, and a major part of water are distilled off. Thereafter, the remaining water and 4-hydroxybutyraldehyde are distilled off at a temperature of up to 100° C. Then, the butanediols are evaporated from the high-boiling fraction at a temperature of up to 180° C., preferably up to 170° C. Finally, MPG and 1,4-BG are separated by distillation.

By employing the combination of the three steps according to the invention, the heating at a high temperature can be avoided in the state where nickel and 4-hydroxybutyraldehyde exist. In addition, the formation of impurities, such as HMPTHF and HBTHF, which deteriorate the separability of the butanediols and which reduce the purity of the products, and the formation of offensive smell-emitting substances, can be prevented. Thus, the unsolved problems in the prior art can be overcome and high-quality MPG and 1,4-BG can be obtained.

The following examples will further illustrate the present invention.

EXAMPLE 1

A product obtained by a hydroformylation reaction of allyl alcohol was extracted with water and then hydrogenated, in the presence of Raney nickel, to obtain an aqueous solution containing 30 ppm of nickel. The aqueous solution was adjusted to pH 9.5 with a 1% aqueous NaOH solution, and the solids thus formed were filtered off by a commercially available cartridge filter (MICROWYND Filter D-PPSB; a product of Nihon AMF Co.). The resulting aqueous solution had a nickel content of 3 ppm. Thus, 90% of the nickel dissolved in the solution was separated out.

The aqueous solution was then charged in an azeotropic distillation column for n-propanol and water in order to distill off a low-boiling fraction. The resulting aqueous solution was charged in a vacuum evaporation distillation column and a major part of the water present was distilled off at 50° to 100° C. A liquid sample taken out through the bottom of the column comprised 14.27 wt. % of water, 0.06 wt. % of 4-hydroxybutyraldehyde, 12.87 wt. % of MPG, 71.95 wt. % of 1,4-BG, 0.04 wt. % of HBTHF, 0.68 wt. % of a high-boiling fraction, 0.13 wt. % of other unidentified components and 15 ppm of dissolved nickel.

The liquid was charged in a vacuum distillation column and remaining water and 4-hydroxybutyraldehyde were distilled off. 14.3% of the liquid charged was distilled off through the top of the column at 39° C. under 50 mmHg. Half of the distillate was refluxed back into the column. The resulting distillate comprised 0.42 wt. % of 4-hydroxybutyraldehyde, a trace of MPG, 0.02 wt. % of other unidentified substances and 99.56 wt. % of water. Neither water nor 4-hydroxybutyraldehyde was detected in the bottom liquid. The column bottom temperature was 157° C. The liquid in the column was analyzed and it was found that no 4-hydroxybutyraldehyde was present in zones of temperatures of 80° C. or higher. The liquid taken out through the bottom comprised 15.0 wt. % of MPG, 84.0 wt. % of 1,4-BG, 0.05 wt. % of HBTHF and 0.79 wt. % of a high-boiling fraction. By-products were scarcely observed in the column.

The liquid was charged into a subsequent vacuum distillation column to separate the high-boiling fraction. The column top pressure was 50 mmHg. A liquid comprising 15.3 wt. % of MPG, 84.5 wt. % of 1,4-BG, 0.05 wt. % of HBTHF and 0.15 wt. % of other components was distilled off in an amount of 97.9%, based on the charged liquid. One-tenth of the distillate was refluxed back into the column. A liquid comprising 0.33 wt. % of MPG, 61.6 wt. % of 1,4-BG, 0.01 wt. % of HBTHF and 38.0 wt. % of a high-boiling fraction was taken out through the bottom of the column at 170° C. The formation of 4-hydroxybutyraldehyde or by-products, such as HBTHF, in the reaction system was scarcely observed.

The liquid distilled through the column top was charged in a vacuum distillation column to separate MPG and 1,4-BG. Based on the total amount of the charged liquid, 15.4 wt. % of a liquid was distilled off through the top of the column at 133° C. under 50 mmHg pressure. The liquid was refluxed into the column in an amount of 8 times as much as the amount of the distillate. The temperature and pressure at the column bottom were 165° C. and 93 mmHg, respectively. The MPG product thus distilled had a purity of 98.9% and a 1,4-BG content of 0.1 wt. %. The 1,4-BG product had a purity of 99.8%, an MPG content of 0.1 wt. % and an HBTHF content of 0.06 wt. %. Both products were substantially odorless.

COMPARATIVE EXAMPLE 1

An aqueous solution was obtained by extracting a hydroformylation reaction product of allyl alcohol with water and then hydrogenating the same in the presence of a Raney nickel catalyst, which solution contained 60 ppm of nickel dissolved therein. The solution was charged into a rotary evaporator. A low-boiling fraction comprising n-propanol and water was distilled off at a temperature of up to 100° C. under a reduced pressure of 5 mmHg to obtain a light green liquid containing 250 ppm of nickel. The liquid was charged in a glass Oldershaw column at a rate of 315 g/h and vacuum distillation was carried out. After initiation of the charging, the zone below the charging position in the column gradually became colored black. After about 2.0 l of the liquid had been charged, the plates in the column became clogged and further distillation became impossible. A black film was formed on the walls of the column.

EXAMPLE 2

The same aqueous solution as in Comparative Example 1 obtained after the hydrogenation reaction was adjusted to pH 9.5 with NaOH. The resulting precipitate was filtered with a filter paper to obtain a filtrate having a nickel content of 3 ppm. The liquid was treated in the same manner as in Comparative Example 1 to distill off a low-boiling fraction and water. The resulting liquid was charged in a glass Oldershaw column at 315 g/h and vacuum evaporation was carried out. A liquid comprising 0.1 wt. % of MPG, 0.02 wt. % of HBTHF and, as the main component, 1,4-BG containing a high-boiling fraction was taken out through the bottom of the column at a rate of 230 g/h at 170° C. The bottom liquid was slightly turbid but substantially free of smell. After the continuous operation for 18 h, no staining was recognized in the column and the flask.

COMPARATIVE EXAMPLE 2

The aqueous solution obtained in Example 2 comprising 0.1 wt. % of MPG, 0.02 wt. % of HBTHF and, as the main component, 1,4-BG containing a high-boiling fraction was charged in a glass Oldershaw column at a rate of 270 g/h and vacuum distillation was carried out. No liquid was taken out through the bottom and, therefore, the bottom temperature was gradually elevated from 170° C. as the high-boiling fraction was concentrated and reached 193° C. after continuous operation for 10 h. The column top temperature was kept constant at 151° C. during the operation under 50 mmHg pressure for 10 h. However, an irritating smell was gradually emitted from the distillate over time. The distillate contained 0.1 wt. % of HBA and the HBTHF content was increased to 0.09 wt. %.

COMPARATIVE EXAMPLE 3

A hydrogenation reaction liquid obtained in the same manner as described in Comparative Example 1 was adjusted to pH 9.5 with a 1% aqueous NaOH solution. The solids thus precipitated were filtered off by a commercially available cartridge filter to obtain an aqueous butanediol solution. Low-boiling substances such as n-propanol were distilled out of the solution to obtain a liquid comprising 85.2 wt. % of water, 0.05 wt. % of HBA, 0.02 wt. % of HBTHF, 1.77 wt. % of MPG and 12.88 wt. % of 1,4-BG. This liquid was charged in a packed column at a rate of 18.0 kg/h and water was distilled off under the atmospheric pressure. About 15.0 kg/h of a liquid substantially comprising water was distilled off through the column top and an equal quantity of the liquid was refluxed back into the column. The column bottom temperature was 135° C. About 3 kg/h of the liquid was taken out through the bottom. The liquid product comprised 9.94 wt. % of water, 0.05 wt. % of HBA, 0.58 wt. % of HBTHF, 10.80 wt. % of MPG and 78.59 wt. % of 1,4-BG. About 83% of HBA reacted to form HBTHF.

EXAMPLE 3

An aqueous solution obtained by pH adjustment, removal of the precipitates and distillation of the low-boiling fraction in the same manner as in Comparative Example 3 was charged in a vacuum evaporator under 150 mmHg, and water was distilled off. The reboiler temperature was 85° C. A liquid taken out from the bottom of the column at a rate of 150 g/h comprised 9.17 wt. % of water, 0.13 wt. % of HBTHF, 9.28 wt. % of MPG and 81.42 wt. % of 1,4-BG. A liquid distilled at a rate of 850 g/h containing water as its main component further contained 0.06 wt. % of HBA, 0.45 wt. % of MPG and 0.84 wt. % of 1,4-BG. HBA was scarcely denatured and HBTHF formation was not recognized.

The embodiments of the invention in which an exclusive property or privilege is claimed are defined as follows:

1. In a process for the preparation of butanediols including the steps of hydroformylation of allyl alcohol, hydrogenation of an aqueous solution of the hydroformylated product and evaporation, in the presence of a nickel catalyst, to form an aqueous mixture containing 2-methyl-1,3-propanediol, 1,4-butanediol and a high-boiling fraction comprising substances having higher boiling points than said 2-methyl-1,3-propanediol and said 1,4-butanediol, the improvement which comprises:
    (1) adjusting the pH of said aqueous mixture to 8.5 or above whereby to form a precipitate and removing thus-formed precipitate from the mixture;
    (2) then distilling off a fraction comprising water and residual 4-hydroxybutyraldehyde from said aqueous mixture at a temperature of up to 100° C.; and
    (3) then heating the resulting mixture to a temperature of up to 180° C. and distilling off 1,4-butanediol and 2-methyl-1,3-propanediol therefrom.

2. A process as claimed in claim 1, wherein said resulting mixture is essentially free of 2-(3-hydroxy-2-methylpropoxy) tetrahydrofuran and 2-(4-hydroxybutoxy)tetrahydrofuran.

3. A process as claimed in claim 1, wherein the pH of said aqueous solution is adjusted to at least 9.5.

4. A process as claimed in claim 1, further comprising a step of distilling said aqueous mixture, after step (1) and prior to step (2), at atmospheric or slightly reduced pressure, to remove not more than 90% of the water in said aqueous mixture, and then reducing the distillation pressure to effect said step (2) of distilling said fraction comprising water and 4-hydroxybutyraldehyde from said aqueous mixture.

5. A process as claimed in claim 1, wherein said step (2) is carried out at a temperature in the range of 50 to 70° C.

6. A process as claimed in claim 1, wherein said high-boiling fraction comprises aldehyde condensates produced in said hydroformylation and hydrogenation steps.

7. A process as claimed in claim 6, wherein said high-boiling fraction is present in an amount of from 0.5 to 1.0% based on the total amount of said 1,4-butanediol and said 2-methyl-1,3-propanediol.

8. A process as claimed in claim 1, wherein in said step (3) said 1,4 butanediol and 2-methyl-1,3-propanediol are distilled by thin film evaporation.

9. A process as claimed in claim 1, wherein, after said step (1), said solution is introduced into a distillation column operated under conditions such that said step (2) is carried out at the upper portion of said distillation column, said resulting mixture flowing down to the bottom of said distillation column at which said step (3) is carried out.

10. A process as claimed in claim 1, wherein in said step (3), said resulting mixture is heated to a temperature in the range of from 133° to 162° C.

11. A process for the separation of 2-methyl-1,3-propanediol and 1,4-butanediol from an aqueous solution thereof, said aqueous solution further containing small amounts of nickel and 4-hydroxybutyraldehyde as impurities therein, and a high-boiling fraction consisting of substances having higher boiling points than said 1,4-butanediol and said 2-methyl-1,3-propanediol, also present as impurities therein, comprising:

adjusting the pH of said aqueous solution to 8.5 or above whereby to form a precipitate containing said nickel;

then removing from said solution the precipitate formed by said pH adjusting step, thereby reducing the nickel content of said solution;

then distilling from said solution at a temperature of up to 100° C. a fraction comprising water and 4-hydroxybutyraldehyde whereby to form a mixture consisting essentially of said 2-methyl-1,3-propanediol, 1,4-butanediol and said high-boiling fraction, said mixture being essentially free of water;

then heating said mixture to a temperature of up to 180° C. to distill off said 2-methyl-1,3-propanediol and 1,4-butanediol therefrom; and then distilling the resulting mixture of 1,4-butanediol and 2-methyl-1,3-propanediol to separately obtain substantially pure 2-methyl-1,3-propanediol and substantially pure 1,4-butanediol.

12. A process for the preparation of 2-methyl-1,3-propanediol and 1,4-butanediol, comprising:

hydroformylating allyl alcohol to form a first reaction mixture containing 4-hydroxybutyraldehyde and 3-hydroxy-2-methylpropionaldehyde and extracting same with water to obtain an aqueous solution of 4-hydroxybutyraldehyde and 3-hydroxy-2-methylpropionaldehyde;

then hydrogenating said aqueous solution of 4-hydroxybutyraldehyde and 3-hydroxy-2-methylpropionaldehyde in the presence of a nickel catalyst, to form an aqueous solution containing 2-methyl-1,3-propanediol, 1,4-butanediol, and impurities, said impurities including nickel, 4-hydroxybutyraldehyde, and a high-boiling fraction consisting of substances having higher boiling points than said 1,4-butanediol and said 2-methyl-1,3-propanediol;

then adding an alkali to said aqueous solution to adjust the pH of said aqueous solution to 8.5 or above whereby to form a precipitate;

then removing from said solution the precipitate formed by said alkali addition step, thereby reducing the nickel content of said solution;

then distilling from said solution at temperatures of up to 100° C. a fraction comprising water and 4-hydroxybutyraldehyde whereby to form a second mixture consisting essentially of said butanediols and remaining impurities, said mixture being essentially free of water;

then heating said second mixture to a temperature of up to 180° C. to distill off said 2-methyl-1,3-propanediol and said 1,4-butanediol; and then separating said 1,4-butanediol from said 2-methyl-1,3-propanediol.

* * * * *